United States Patent
Fish et al.

(10) Patent No.: US 11,348,685 B2
(45) Date of Patent: May 31, 2022

(54) SYSTEM AND METHOD FOR A TELEMEDICINE DEVICE TO SECURELY RELAY PERSONAL DATA TO A REMOTE TERMINAL

(71) Applicant: 19LABS INC., Redwood City, CA (US)

(72) Inventors: Ram Adva Fish, Redwood City, CA (US); Gerald Charles Horel, Redwood City, CA (US)

(73) Assignee: 19Labs, Inc., San Mateo, CA (US)

( * ) Notice: Subject to any disclaimer, the term of this patent is extended or adjusted under 35 U.S.C. 154(b) by 209 days.

(21) Appl. No.: 15/721,978

(22) Filed: Oct. 2, 2017

(65) Prior Publication Data

US 2018/0247029 A1 Aug. 30, 2018

Related U.S. Application Data

(60) Provisional application No. 62/465,066, filed on Feb. 28, 2017.

(51) Int. Cl.
*G16H 40/67* (2018.01)
*H04L 9/40* (2022.01)
(Continued)

(52) U.S. Cl.
CPC ............ *G16H 40/67* (2018.01); *G16H 15/00* (2018.01); *G16H 80/00* (2018.01);
(Continued)

(58) Field of Classification Search
CPC ........ G16H 40/67; G16H 15/00; G16H 80/00; H04L 63/0281; H04L 63/04;
(Continued)

(56) References Cited

U.S. PATENT DOCUMENTS

| 2005/0198379 A1* | 9/2005 | Panasyuk | H04L 69/329 |
| | | | 709/239 |
| 2009/0222891 A1* | 9/2009 | Heffez | H04L 63/0853 |
| | | | 726/3 |

(Continued)

OTHER PUBLICATIONS

Garg, Vaibhav and Brewer, Jeffery, Telemedicine Security: A Systematic Review, 5 Journal of Diabetes Science and Technology (Year: 2001).*

(Continued)

*Primary Examiner* — Evangeline Barr
*Assistant Examiner* — Jordan L Jackson
(74) *Attorney, Agent, or Firm* — Inventive Law Inc.; Jim H. Salter

(57) ABSTRACT

A method for securely relaying personal data between a telemedicine device and a remote terminal via a proxy server includes establishing a communication link between the telemedicine device and the proxy server over a first communication network. A request, including authentication access data, is received from a remote terminal for a remote user to assess personal data of a telemedicine device user. Upon validating the authentication access data to approve access to the personal data on the telemedicine device by the remote user, the personal data is relayed between the telemedicine device and the remote terminal in a remote assess session while preventing secure personal data of the telemedicine device user from being sent to the proxy server. If the telemedicine device communicates over a second communication network, the communication link is re-established with the proxy server over the second communication network without terminating the remote access session.

32 Claims, 7 Drawing Sheets

(51) Int. Cl.
*H04W 12/02* (2009.01)
*G16H 15/00* (2018.01)
*G16H 80/00* (2018.01)

(52) U.S. Cl.
CPC .......... *H04L 63/0281* (2013.01); *H04L 63/04* (2013.01); *H04L 63/0442* (2013.01); *H04L 63/101* (2013.01); *H04L 63/107* (2013.01); *H04W 12/02* (2013.01)

(58) Field of Classification Search
CPC .. H04L 63/101; H04L 63/0442; H04W 12/02; G06F 19/3418
See application file for complete search history.

(56) References Cited

U.S. PATENT DOCUMENTS

| | | | | |
|---|---|---|---|---|
| 2012/0310410 | A1* | 12/2012 | Adams | G06Q 10/087 700/237 |
| 2014/0101273 | A1* | 4/2014 | Logan | G16H 30/20 709/206 |
| 2014/0379120 | A1* | 12/2014 | Heffron | G07F 11/62 700/214 |
| 2015/0317456 | A1* | 11/2015 | Olson | A47B 67/02 700/241 |
| 2015/0379198 | A1* | 12/2015 | Tambasco, Jr. | G16H 10/60 705/3 |
| 2016/0132662 | A1* | 5/2016 | Paradissis | G06F 17/00 700/244 |
| 2016/0246936 | A1* | 8/2016 | Kahn | G16H 80/00 |
| 2017/0041296 | A1* | 2/2017 | Ford | G06F 16/951 |

OTHER PUBLICATIONS

Michael Ammann, Design and Implementation of a Peer-to-Peer based System to enable the Share Functionality in a Platform-independent Cloud Storage Overlay, University of Zurich Master Thesis (Jan. 31, 2013) (Year: 2013).*

Maji et al., Security Analysis and Implementation of Web-based Telemedicine Services with a Four-tier Architecture, 2008 Second International Conference on Pervasive Computing Technologies for Healthcare (Jul. 22, 2008) (Year: 2008).*

Lim et al., SNMP-Proxy For Wireless Sensor Network, Fifth International Conference on Information Technology: New Generations 738-743 (Year: 2008).*

Secure Remote Desktop Solutions for Healthcare Institutions, Proxy Networks (web archive captured on Oct. 29, 2015) (Year: 2015).*

Warren et al., OdinTelehealth: A Mobile Service Platform for Telehealth, 5 Procedia Computer Science—ScienceDirect 681-688 (Year: 2011).*

Chryssanthou et al., Security and trust in virtual healthcare communities, Conference: Proceedings of the 2nd International Conference on Pervasive Technologies Related to Assistive Environments, PETRA 2009, Corfu, Greece (Jun. 2009) (Year: 2009).*

Jang-Jaccard et al., WebRTC-based video conferencing service for telehealth, 98 Computing 169-193 (Year: 2016).*

* cited by examiner

SYSTEM AND METHOD FOR A TELEMEDICINE DEVICE TO SECURELY RELAY PERSONAL DATA TO A REMOTE TERMINAL

CROSS REFERENCE TO RELATED APPLICATIONS

The present invention claims the priority benefit of U.S. Provisional Patent Application No. 62/465,066 filed on Feb. 28, 2017, which is incorporated in its entirety herein by reference.

FIELD OF THE INVENTION

The present invention relates to telemedicine devices. More specifically, the present invention relates to system and method for a telemedicine device to securely relay personal data to a remote terminal.

BACKGROUND OF THE INVENTION

Telemedicine describes the use of telecommunication and information technology to provide clinical health care. Telemedicine may be used to provide improved access to medical services in distant rural communities where normal health care services may not be consistently available. Telemedicine may also save lives in emergency situations at remote locations, which lack normal, regular health care services. Telemedicine devices may be deployed at remote locations and/or in remote clinics and/or in private homes for use by individual patients, for example, with medical conditions requiring continuous connectivity to health care professionals.

During the use of a telemedicine device, there may be many transactions between a patient and a health care professional. For example, a patient may feel ill and call a doctor via the telemedicine device using a video call. The telemedicine device may upload the patient's private medical data, and provide measured data from diagnostic devices over a communication network to a remote user, such as a doctor. The doctor may observe the patient over the video call and may analyze the patient's private medical data at a remote terminal.

However, transferring the patient's private medical data over the communication network, such as the internet, for example, may present opportunities for rogue interception and rogue use of the patient's private medical data. Thus, it may be desirable to have methods and systems for securely sharing a patient's private medical data over a communication link with a remote user.

SUMMARY OF THE INVENTION

There is thus provided, in accordance with some embodiments of the present invention, a method for a telemedicine device to securely relay personal data to a remote terminal via a proxy server. The method may include, by a processor in a telemedicine device, establishing a communication link with a proxy server over a first communication network. A request, including authentication access data, may be received via the proxy Server over the communication link from a remote terminal for a remote user to assess personal data of a telemedicine device user. Upon validating the authentication access data to allow the remote user access to the personal data on the telernedicine device, the personal data may be relayed between the telemedicine device and the remote terminal via the proxy server over the communication link in a remote assess session while preventing secure personal data of the telemedicine device User stored on the telemedicine device from being sent to the proxy server over the communication link. If the telemedicine device communicates over a second communication network, the communication link may be re-established with the proxy server over the second communication network without terminating the remote access session, where the personal data relayed between the telemedicine device and the remote terminal via proxy server may be encrypted.

Furthermore, in accordance with some embodiments of the present invention, the secure personal data of the telemedicine device user may include protected health information (PHI) or personally identifiable information (PII) data of the telemedicine device user.

Furthermore, in accordance with some embodiments of the present invention, the first communication network and the second communication network may be selected from a group consisting of a wireless fidelity (Wi-Fi) network, a cellular network, a wired network, and a Bluetooth network.

Furthermore, in accordance with some embodiments of the present invention, establishing the communication link with the proxy server may include establishing the communication link with the proxy server in response to a call made from the telemedicine device user to the remote user.

Furthermore, in accordance with some embodiments of the present invention, the method may include alerting the telemedicine device user that the remote user requested access to the personal data.

Furthermore, in accordance with some embodiments of the present invention, validating the authentication access data may include allowing the telemedicine device user to approve the access to the personal data in response to alerting the telemedicine device user.

Furthermore, in accordance with some embodiments at the present invention, validating the authentication access data may include assessing that the remote user is not located within a restricted geographical area.

Furthermore, in accordance with some embodiments of the present invention, validating the authentication access data may include assessing that the remote user is not on a list of restricted users.

Furthermore, in accordance with some embodiments of the present invention, validating the authentication access data may include comparing an IP address of the remote terminal to an IP address associated with a remote voice communication or video communication of the remote user.

Furthermore, in accordance with some embodiments of the present invention, the method may include requesting, a secondary authentication upon assessing that the IP address of the remote terminal and the IP address associated with the remote voice communication or the video communication of the remote user do not match.

There is further provided, in accordance with some embodiments of the present invention, a method for a proxy server to manage relaying personal data between a telemedicine device and a remote terminal. The method may include, by a processor in a proxy server, establishing a first communication link with a telemedicine device over a first communication network. A request may be received from a remote terminal for a remote user to access to personal data of a telemedicine device user of the telemedicine device. In response to the receiving the request, a secure proxy uniform resource locator (URL) may be sent to the remote terminal. Upon activating the secure proxy URL on the remote terminal by the remote user, authentication access data from the remote terminal may be received. Upon validating the authentication access data, a second communication link with the remote terminal may be established, and the authentication access data may be sent to the telemedicine device over the first communication link. Upon the telemedicine device allowing access to the personal data by the remote user, a remote access session may be established so as to enable relaying the personal data between the telemedicine device and the remote terminal over the first and second communication links, where the personal data relayed between the telemedicine device and the remote terminal over the first and second communication links may be encrypted.

Furthermore, in accordance with some embodiments of the present invention, the method may include upon assessing that the telemedicine device communicates over a second communication network, re-establishing the first communication link with the telemedicine device over the second communication network without terminating the remote access session.

Furthermore, in accordance with some embodiments of the present invention, establishing the first communication link with the telemedicine device may include establishing the first communication link in response to a call made from the telemedicine device user to the remote user.

Furthermore, in accordance with some embodiments of the present invention, the method may include terminating the remote access session and deactivating the secure proxy URL in response to the telemedicine device user or the remote user ending a call.

Furthermore, in accordance with some embodiments of the present invention, the method may include terminating the remote access session and deactivating the secure proxy URL after a predefined duration or inactivity time.

Furthermore, in accordance with some embodiments of the present invention, sending the secure proxy URL, may include sending multiple unique secure proxy URLs respectively to multiple remote terminals.

Furthermore, in accordance with some embodiments of the present invention, the authentication access data may include a token encrypted at the remote terminal using a public key of the telemedicine device.

Furthermore, in accordance with some embodiments of the present invention, the token may be signed using a key known by the proxy server.

There is further provided, in accordance with some embodiments of the present invention, a telemedicine device for securely relaying personal data to a remote terminal via a proxy server may include a memory and a processor. The processor may be configured to establish a communication link with a proxy server over a first communication network, to receive via the proxy server over the communication link, a request, including authentication access data, from a remote terminal for a remote user to assess personal data of a telemedicine device user, upon validating the authentication access data to allow the remote user to access to the personal data on the telemedicine device, to relay the personal data between the telemedicine device and the remote terminal via the proxy server over the communication link in a remote assess session while preventing secure personal data of the telemedicine device user stored on the telemedicine device from being sent to the proxy server over the communication link, and if the telemedicine device communicates over a second communication network, to re-establish the communication link with the proxy server over the second communication network without terminating the remote access session, where the personal data relayed between the telemedicine device and the remote terminal via proxy server may be encrypted.

Furthermore, in accordance with some embodiments of the present it the secure personal data of the telemedicine device user may include protected health information (PHI) or personally identifiable information (PII) data of the telemedicine device user.

Furthermore, in accordance with some embodiments of the present invention, the first communication network and the second communication network may be selected from a group consisting of a wireless fidelity (Wi-Fi) network, a cellular network, a wired network, and a Bluetooth network.

Furthermore, in accordance with some embodiments of the present invention, the processor may be configured to establish the communication link with the proxy server in response to a call made from the telemedicine device user to the remote user.

Furthermore, in accordance with some embodiments of the present invention, the telemedicine device may include a video camera, and where the call may include a video call.

Furthermore, in accordance with some embodiments of the present invention, the telemedicine device may include an input device for receiving inputs from the telemedicine device user, and an output device for displaying information to the telemedicine device user.

Furthermore, in accordance with some embodiments of the present invention, the input device and the output device may include a touch screen.

Furthermore, in accordance with some embodiments of the present invention, the processor may be configured to alert the telemedicine device user on the output device that the remote user requested access to the personal data.

Furthermore, in accordance with some embodiments of the present invention, the processor may be configured to validate the authentication access data by allowing the telemedicine device user to approve access to the personal data on the input device response to the alert.

Furthermore, in accordance with some embodiments of the present invention, the processor may be configured to validate the authentication access data by assessing that the remote user is not located within a restricted geographical area.

Furthermore, in accordance with some embodiments of the present invention, the processor may be configured to validate the authentication access data by assessing that the remote user is not on a list of restricted users.

Furthermore, in accordance with some embodiments of the present invention, the processor may be configured to validate the authentication access data by comparing an IP address of the remote terminal to an IP address associated with a remote voice communication or video communication of the remote user.

Furthermore, in accordance with some embodiments of the present invention, the processor may be configured to request a secondary authentication upon assessing that the IP address of the remote terminal and the IP address associated with the remote voice communication or the video communication of the remote user do not match.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention.

DETAILED DESCRIPTION OF THE INVENTION

Figure 1:
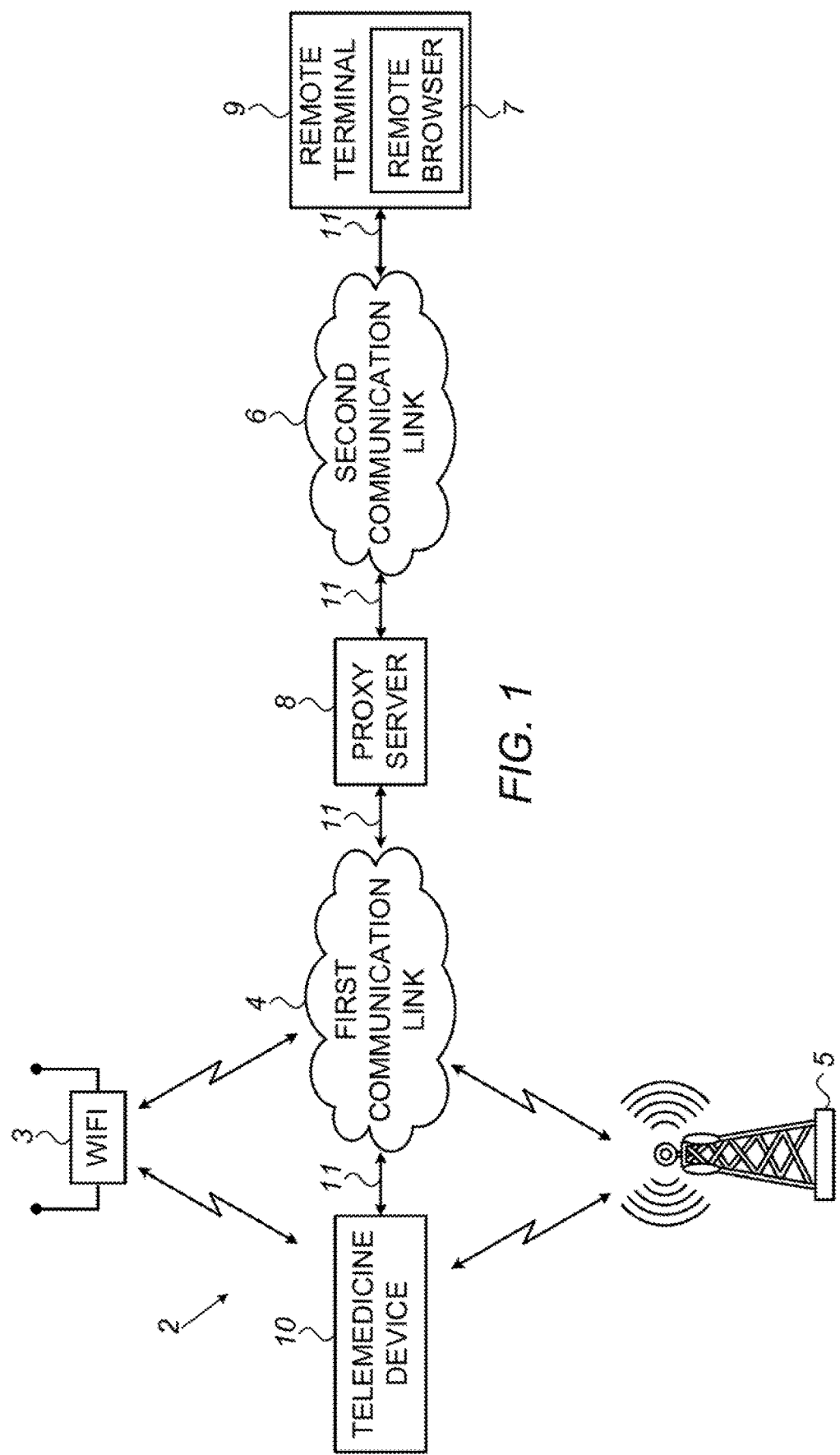
FIG. 1 illustrates a block diagram of a system for securely sharing personal data of a user of a telemedicine device with a remote terminal via a proxy server, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Some embodiments of the present invention described herein pet vide systems and methods for securely sharing personal data of a user of a telemedicine device over a communication network to a remote user via a proxy server. For example, a user of the telemedicine device (e.g., feeling ill) may place a call (e.g., a yoke call and/or a video call) to a remote user, such as a doctor and/or any health care profession, and/or provider. In response to the call, the remote user may request via a proxy server to remotely view the personal data of the telemedicine device user on a remote browser operating on a remote terminal.

In response to the request, the proxy server may validate whether the remote user is authorized to view the personal data and may also determine if the telemedicine device is connected to the proxy server. The proxy server may then forward the request to the telemedicine device user by the remote user to communicate with the remote user at the remote terminal. The telemedicine device may validate whether the remote user is authorized to view the personal data of the telemedicine device user. Once the telemedicine device approves access to the personal data by the remote user, the proxy server may initiate a remote access session between the telemedicine device and the remote terminal. In the remote access session, the personal data, typically encrypted, may be relayed between the two endpoints (e.g., the telemedicine device and the remote terminal) via the proxy server, which manages the data now between the two endpoints.

In some embodiments of the present invention, the personal data may be encrypted using transport layer security (TLS), for example, and may be relayed and/or transmitted over a TLS encrypted socket. In other embodiments, any suitable transmission mechanism (e.g., secure communication protocols) may be used which operates using mutual authentication at the endpoints of both sides of the communication link. Furthermore, the secure communication protocol may be based on establishing a trusted relationship between two endpoints in the system.

The doctor may decide to obtain records of the user of the telemedicine device (e.g., a patient) that may be stored on the telemedicine device. In trying to diagnose the problem of the patient, the doctor may tell the patient to use diagnostic devices stored in the telemedicine device such as a blood pressure meter, for example. Real-time diagnostic measurements may be taken, encrypted and relayed to the doctor s the communication link. In response, the doctor may request that the patient take certain medications stored in the telemedicine device and/or the doctor may call emergency services to dispatch an ambulance, for example, to the location of the telemedicine device (e.g., the patient). All of the personal medical data related to the telemedicine device user, diagnostic measurements, and/or doctor reports may be stored in the telemedicine device (e.g., in a memory).

In the embodiments of the present invention described herein, the telemedicine device may communicate with the proxy server over a first communication link, and the remote terminal may communicate with the proxy server over a second communication link. A communication link in the context of this patent application may be a connection for communicating data, video, and/or voice between any two elements in the systems shown in the figures herein. A communication link may include routing the personal data over one path between the endpoints or over multiple paths between the endpoints.

After the remote user at the remote terminal are validated and/or authenticated, the proxy server may establish and/or maintain a remote access session between the telemedicine device and the remote terminal. While the remote access session remains active, encrypted personal data may then be relayed between the telemedicine device and the proxy server via the first communication link. The encrypted personal data may then be relayed between the proxy server and the remote terminal via the second communication link, in the embodiments of the present invention, the proxy server may be used to manage relaying the personal data between the telemedicine device and the remote user.

In some embodiments, the telemedicine device may be used to monitor a patient that is moving between different locations or areas where medical treatments take place, such as from the operating room to an intensive care unit, for example. In the following exemplary scenario, the telemedicine device may be placed on the gurney of the patient to allow a remote user (e.g., a doctor) to continuously monitor the patient during movement between different locations. The gurney may be wheeled from the operating room where the telemedicine device may be initially operating on a local Wi-Fi network in a first building to the intensive care unit in a second building. The telemedicine device initially operating over Wi-Fi near the operating room, may decide (e.g., due to issues related to quality of service of the communication network, signal strength, cost, and/or other network metrics) to switch to a cellular network (e.g., a second communication network) as the gurney is wheeled between the first and second buildings where the initial Wi-Fi signal may be too weak, for example. When the gurney enters the intensive care unit in the second building, the telemedicine device may choose to operate on another Wi-Fi network operating, in the area of the intensive care unit.

In this exemplary scenario, the telemedicine device communicated with the remote user over three different communication networks (a first Wi-Fi network in the first building, a cellular network between buildings, and the second Wi-Fi network in the second building). A doctor at a remote terminal may monitor the patient during the patient's movement on the gurney between buildings. With normal point-to-point communication networks, the communication link would have disconnected as the telemedicine device switched communicating from a first communication network to a second communication network (e.g., from Wi-Fi to a cellular network, for example).

However in the embodiments of the present invention, with the proxy server managing the relay of the personal data between the telemedicine device and the remote user over the first and the second communication links, the proxy server preserves the remote access session as the first communication link drops as the telemedicine device switches communication protocols from Wi-Fi to cellular (e.g., from the first to the second communication network).

For example, the proxy server (e.g., the processor of the proxy server) may be configured to identify the parameters of a specific telemedicine device such as the IP address, media access control (MAC) number (e.g., of the communication circuitry), and/or the serial number of the telemedicine, device monitoring a specific patient in remote communication with a specific doctor at a remote terminal as the telemedicine device switches operation from the first to the second communication network. However, the second communication link between the proxy server and remote terminal may remain unaffected even as the first communication link drops.

Thus, when the first communication link is re-established over the second communication network (e.g., protocol), the proxy server may be configured to quickly identify using the specific telemedicine device parameters, authenticate the same telemedicine device communicating now on the second communication network and re-establish the communication link between the telemedicine device and proxy server in the same remote access session. As a result, the remote user may not even perceive any change in the relay of the personal data (e.g., quality of service) since the proxy server knows how to route the personal data to the remote terminal even as the telemedicine device switched communication protocols and the first communication link had dropped and was re-established.

FIG. 1 illustrates a block diagram of a system 2 for securely sharing personal data of a user of a telemedicine device 10 with a remote terminal 9 via a proxy server 8, in accordance with some embodiments of the present invention. System 2 may include proxy server 8, which may be used to manage relaying the personal data between telemedicine device 10 and a remote browser 7 on remote terminal 9 via a first communication link 4 and a second communication link 6. Telemedicine device 10 may communicate with proxy server 8 over a Wi-Fi communication network 3, a cellular communication network 5, and/or via a wired network 11 in first communication link 4. Although proxy server 8 is shown communication with remote terminal 9 over second communication link 6 with wired connections 11 with the internet, any portions of second communication link 6 may also operate over Wi-Fi, cellular, Bluetooth and/or any other suitable communication network.

A typical point-to-point connection between a client and server communicating over a communication network may be performed by peer-to-peer negotiation initiated by the client, for example. The client negotiates directly with the server endpoint where the negotiation is originated by the client. Furthermore in a typical proxy environment, the proxy negotiates with the client and then initiates a secure connection to the server endpoint.

However in some embodiments of the present invention, telemedicine device 10 may establish a secure connection (e.g., first communication link 4) with proxy server 8. Typically, this may be in response to the telemedicine device user initiating a call (e.g., voice or video call) to the remote user (e.g., the doctor). Establishing the call may be oxer the same communication link, but typically established over a different communication link dedicated for voice and/or video calls. Similarly, remote terminal 9 may establish a secure connection (e.g., second communication link 6) with proxy server 8. In some embodiments, this may be in response to the remote user, such as the doctor having already received the call from the patient. The doctor may need access to the patient's personal data, for example, such as the patient medical history and/or to obtain real time measurements from diagnostic devices and/or sensors connected to the patient and coupled to telemedicine device 10.

In some embodiments, proxy server 8 may determine whether telemedicine device 10 is available for communication and may establish a remote access session to route relay personal data, typically encrypted, between telemedicine device 10 and remote terminal 9 for a remote user to view on remote browser 7. In other embodiments, when proxy server 8 receives a request from the remote user to view the personal data on remote browser 7, proxy server 8 may validate and/or authenticate the remote user and determine whether the remote user may view the personal data before establishing a remote access session between telemedicine device 10 and remote terminal 9.

Alternatively or additionally, telemedicine device 10 may validate and/or authenticate the remote user so as to determine whether to allow access to a remote user at remote terminal 9 to view personal data stored on telemedicine device 10 on remote browser 7 running on remote terminal 9. In some embodiments, upon telemedicine device 10 validating the remote user for access to the personal data, telemedicine device 10 may send an indication, or a notification, to proxy server 8 that the remote user may access the personal data.

In this manner, by using proxy server 8 to manage relaying personal data from telemedicine device 10 to remote terminal 9, proxy server 8 may establish connections across diff rent protocols and behind different network address translation (NAT) enabled routers, for example. This mitigates a variety of potential problems when transitioning, for example, from Wi-Fi to cellular communications or vice versa, which may allow proxy server 8 to change its Internet protocol (IP) address dynamically while remote browser 7 is in a remote access session with telemedicine device 10. In this case, proxy server 8 may re-establish the connection with remote browser 7 and the remote user may experience only a slight intermittent connection drop while the connection is being re-established.

In some embodiments of the present invention, proxy server 8 may preserve the remote access session when the connection that is routing data between the telemedicine device and the proxy server (e.g., first communication link 4) disconnects, and/or when the connection that is routing data between the proxy server and the remote terminal disconnects (e.g., second communication link 6). The proxy server may suspending the data muting until the disconnected connection that is routing data is re-established.

With typical proxy environments, the proxy server address may be preconfigured since system 2 is self-configuring. Proxy server 8 may identify itself on establishment of a connection (e.g., remote access session) with remote terminal 9 using a secure identification mechanism, such as a digitally signed certificate signed by a trusted source, for example.

In some embodiments of the present invention, proxy server 8 may generate and send a proxy uniform resource locator (URL) address to remote terminal 9 using a different communication path, or link. In other embodiments, proxy server 8 may frequently change the proxy URL addresses so as to prevent proxy URI, re-use and maintain system security for managing the patient's personal data. This may help to prevent rogue users at remote terminal 9 to guess the correct server address.

In some embodiments of the present invention, a sessionid may be initiated when a call starts. If the URL generated by proxy server 8 is not activated by the remote user with a predefined duration such as in 10 minutes, for example, or if a session of remote browser is terminated or exited by the remote user, proxy server 8 and/or telemedicine device 10 may be timed out and/or invalidate the URL.

In some embodiments of the present invention, the connection or link (e.g., first communication link 4) may include a websocket protocol from telemedicine device 10 to remote browser 7. The connection between remote browser 7 to proxy server 8 (e.g., second communication link 6) may include hypertext transfer protocol (HTTP) and websocket protocol. In other embodiments, the connection from telemedicine device 10 to remote browser 7 may use hypertext transfer protocol (HTTP). Other protocols, such as WebRTC standard protocols, may also be used to establish and manage the connections between proxy server 8, telemedicine device 10, and the applications running on remote browser 7 of remote terminal 9.

In some embodiments of the present invention, proxy URLs may be protected via HTTP Secure (HTTPS). Authentication tokens may be generated using the sessionid and other data available on telemedicine device 10 such as the identity of the telemedicine device user, device configuration parameters, time, and/or network information. The tokens may be encrypted using the public key of telemedicine device 10 and may be only decrypted by telemedicine device 10. The sessionid of telemedicine device 10 may not be relayed un-encrypted over system 2.

In some embodiments of the present invention, remote terminal 9 may establish an HTTPS session with proxy server 8 (e.g., second communication link 6). Proxy server 8 may determine if a routing (e.g., over first communication link 4) to telemedicine device 10 has been established and is online. Proxy server 8 may relay an authentication token (e.g., authentication access data) over the routing to telemedicine device 10. Telemedicine device 10 may authenticate or validate the authentication token, and send an indication to proxy server 8 so as to permit proxy server 8 to establish a remote access session with telemedicine device 10. Proxy server 8 may relay the indication to remote terminal 9 (e.g., to remote browser 7).

In some embodiments of the present invention, proxy server 8 may authorize the communication routing between remote terminal 9 and telemedicine device 10. The communication routing may include the first communication link 4 and the second communication link 6.

System 2 is shown in FIG. 1 by way of example, and not by way of limitation of the embodiments of the present invention. For example, any number of proxy servers may be used to manage relaying the personal data of the telemedicine device user to a remote user. Any communication link may be used to relay data, voice, and video between elements in the system. The communication networks are not limited to the three communication networks shown in FIG. 1 associated with first communication link 4 between telemedicine device 10 and proxy server 8 (e.g., Wi-Fi 3, cellular 5, or wired 11), but may be any suitable communication network type and/or protocol.

Figure 2:
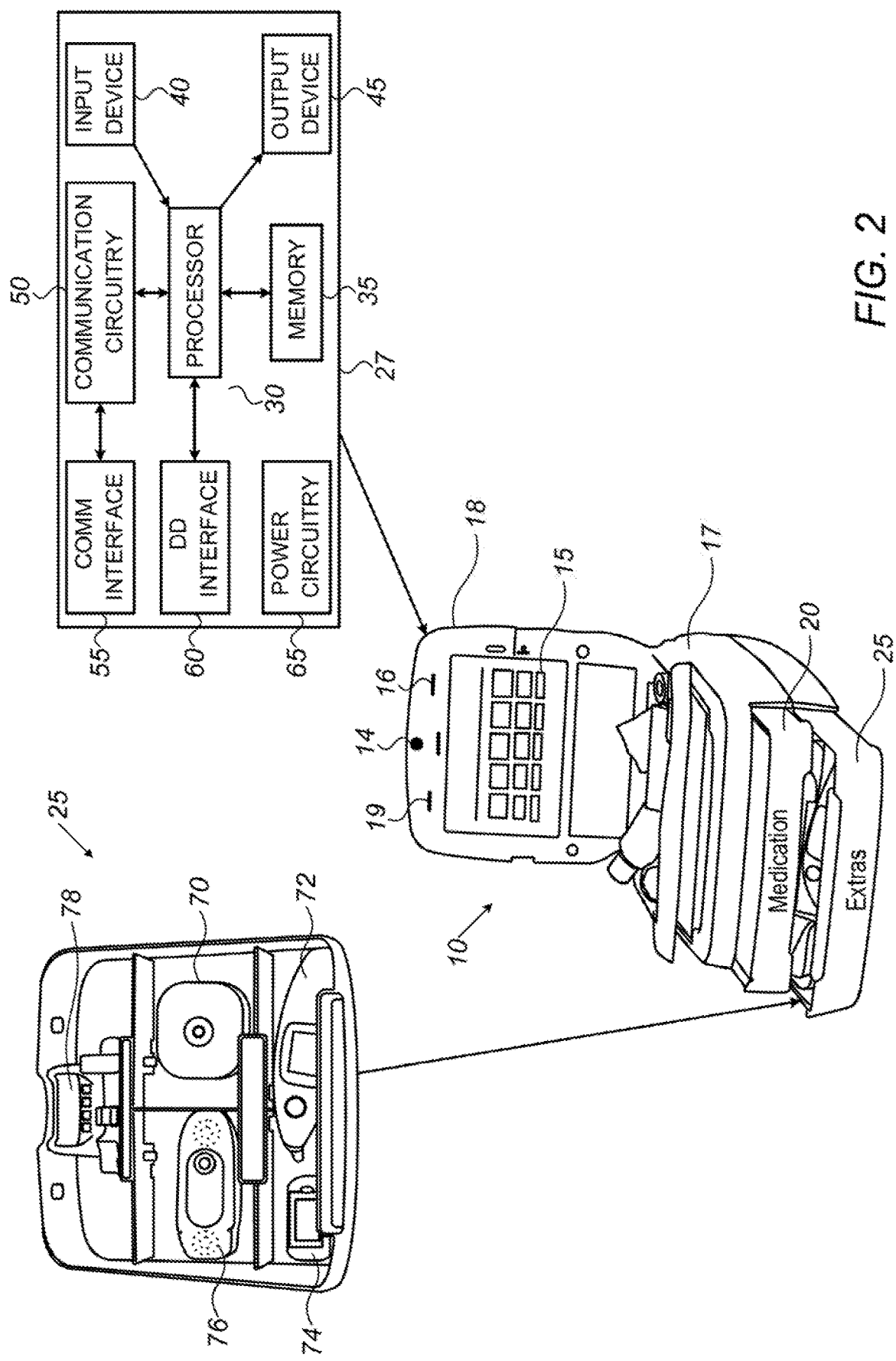
FIG. 2 schematically illustrates a telemedicine device, in accordance with some embodiments of the present invention.

FIG. 2 schematically illustrates telemedicine device 10, in accordance with some embodiments of the present invention. Telemedicine device 10 may include an input/output device, such as a touch screen 15, for example, which may be used by as user of telemedicine device 10 to perform a variety of functions and to communicate with a remote user via communication network 4. Telemedicine device 10 may include a lid 18, which is configured to hold touch screen 15. Lid 18 may be configured to be opened or closed into a housing 17 of telemedicine device 10. Telemedicine device 10 may include a camera 14, such as built-in video camera, for example. Telemedicine device 10 may include audio input 19 and/or output devices 16 such as microphones 19 and/or speakers 16.

In some embodiments of the present invention, telemedicine device 10 may include one or more drawers such as a medication drawer 20 and an accessory drawer 25. In the exemplary embodiment shown in FIG. 2, medication drawer 20 may include medications for the telemedicine device user. Medication drawer 20 may be preloaded with different medications. In some embodiments, telemedicine device 10 may include a lock not shown) so as to keep medicine drawer 20 locked until a remote user such as a doctor may remotely authorize unlocking medicine drawer 20 so as to allow access to a variety of medications by the telemedicine device user.

In some embodiments of the present invention, accessory drawer 25 may store a variety of diagnostic devices and/or sensors, such as a blood pressure meter 70, a thermometer 72, a pulse oximeter 74, an electrocardiogram (ECG) patch 76, and/or extras, such as a splint 78, for example.

Telemedicine device 10 may include electronic components as shown in an inset 27 of FIG. 2. Telemedicine device 10 may include a processor 30, a memory 35, an input device 40, an output device 45, communication circuitry 50, power circuitry 65 (e.g., for powering telemedicine device 10), a communication interface 55, and a diagnostic device (DD) and sensor interface (e.g., circuitry for coupling and/or interfacing the diagnostic devices and/or sensors signals to telemedicine device 10). Communication circuitry 50 may include for example, cellular, and/or Bluetooth circuitry interfaced to an antenna via communication interface 55, for example.

Some embodiments of the present invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

Processor 30 may include one or more processing units, e.g. of one or more computers. Processor 30 may be configured to operate in accordance with programmed instructions stored in memory 35. Processor 30 may be capable of executing an application for sharing personal data stored in memory 35 on telemedicine device 10 with a remote user using remote terminal 9.

Processor 30 may communicate with output device 45. For example, output device 45 may include a computer monitor or screen. Processor 30 may communicate with a screen of output device 45 to display information for the telemedicine device user. In another example, output device 45 may include a printer, display panel, speaker, or another device capable of producing visible, audible, or tactile output.

Processor 30 may communicate with input device 40. For example, input device 40 may include one or more of a keyboard, keypad, or pointing device for enabling a user to inputting data or instructions for operation of processor 30. Touch screen 15, for example, may to provide functionality of both input device 40 and output device 45.

Processor 30 may communicate with memory 35. Memory 35 may include one or more volatile or nonvolatile memory devices. Memory 35 may be utilized to store, for example, programmed instructions for operation of processor 30, data or parameters for use by processor 30 during operation or results of operation of processor 30.

Memory 35 may include a computer readable medium for storing program instructions for operation of processor 30. It is noted that memory 35 and/or any suitable data storage device communicating with processor 30 may be remote from processor 30. Memory 35 may store a module in the form of an installation package or packages that can be downloaded and installed for execution by processor 30. Memory 35 may be utilized to store data or parameters for by processor 30 during operation, or results of operation of processor 30.

In operation, processor 10 may execute a method for sharing personal data stored in memory 35 on telemedicine device 10 with a remote user using remote terminal 9 via proxy server 8.

In some embodiments of the present invention, the personal data referred to herein may include any private and/or confidential medical data of the user of telemedicine device 10 and/or records of any transactions that occurred by any user using telemedicine device 10. Records of any transactions that occurred by any user using telemedicine device 10 may include a log of calls with dates, times, the identification of the remote user such as a clinic and/or a doctor who was connected to the user (e.g., the patient). The personal data may also include real time data such as diagnostic measurements such as blood measurements, blood oximeter measurements, etc. The personal data may be encrypted and sent to the remote user (e.g., a doctor) at the remote terminal for viewing. Note that a heart rate measurement alone is not personal data until it is paired with identifying data of the patient such as the patient's name, for example.

However, the telemedicine device may also store secure personal data related to the user of telemedicine device 10. Secure personal data in the context of this patent application may include, for example, protected health information (PHI) data and/or personally identifiable information (PII) data. PHI data may include individually identifiable health information including demographic data, such as the user's past, present or future physical or mental health or condition, the administration of health care to the user, payments Mated to administering health care to the user, and/or the user's identity. PH data may include information which can be, used to distinguish or trace the user's identity, such gas the user's name, Social Security Number, biometric records, date and place of birth, mother's maiden name, driver's license number, account numbers, credit or debit card numbers, and/or any information providing access to the user's financial account such, access codes and/or passwords.

In some embodiments of the present invention, processor 30 may be configured to prevent the secure personal data of the telemedicine device user stored on telemedicine device 10 from being sent to proxy server 8 over the communication link 4. In some embodiments, for example, processor 30 may prevent the secure personal data from being sent out of the telemedicine device by encrypting the secure personal data with strong encryption using a private key of the telemedicine device, which may be placed in the key storage of the telemedicine device. Thus, even if a rogue user does manage to intercept the secure personal data stored on the telemedicine device, the rogue user will be unable to decrypt the secure personal data.

In some embodiments of the present invention, processor 30 may be configured to erase PHI data of the user after each session.

In some embodiments of the present invention, telemedicine device 10 may include a touchscreen 15, a handheld device, such as a smartphone, or a tablet device for performing the functions herein. In other embodiments, telemedicine device 10 may include a large, fixed (e.g., not mobile) terminal with large cabinets for holding large van ties of medications, diagnostic devices or sensors, all of which controlled remotely by a remote user such as a doctor.

Figure 3:
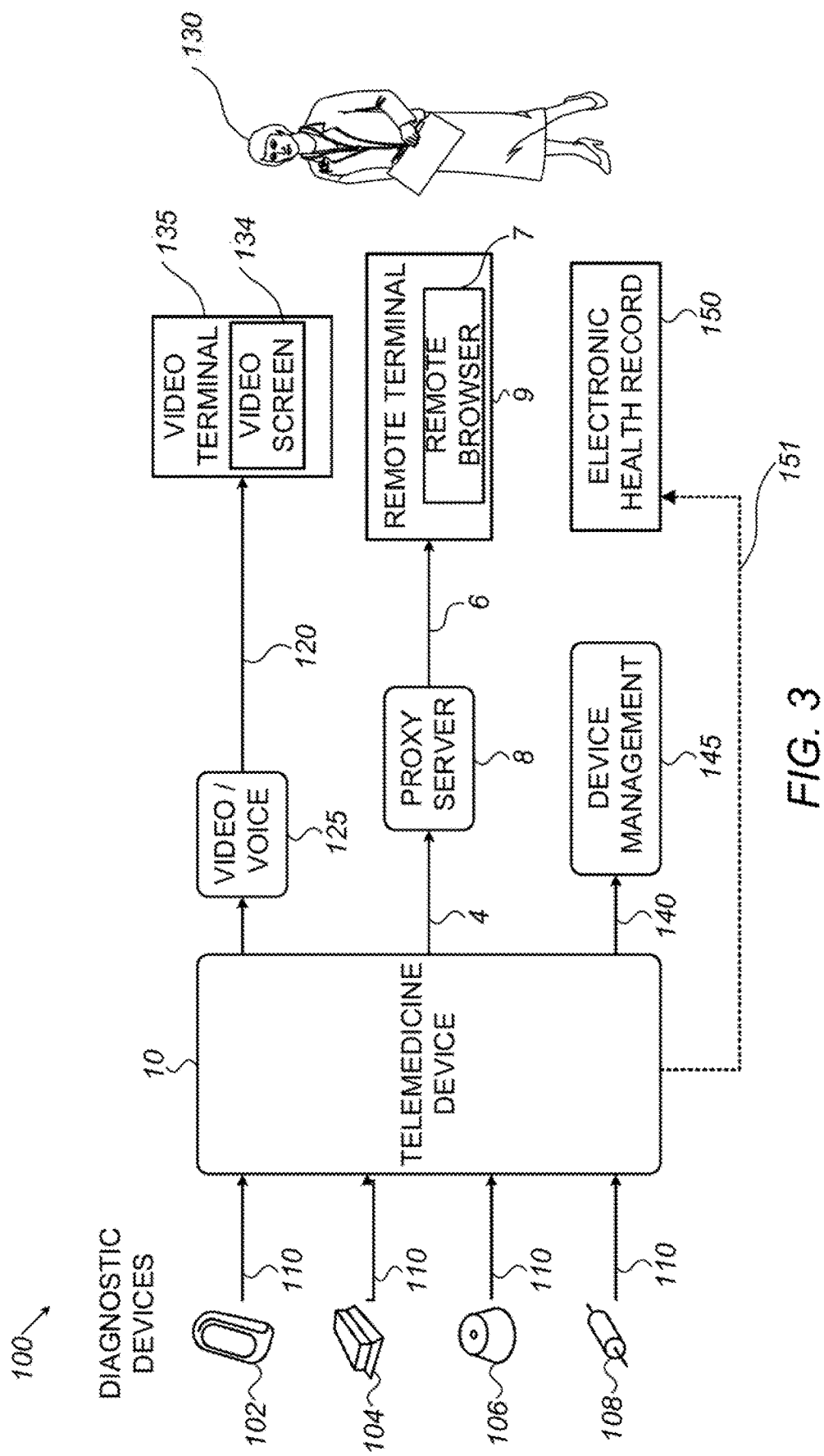
FIG. 3 schematically illustrates a block diagram of a system for managing personal data relayed between telemedicine device and a remote user, in accordance with some embodiments of the present invention.

FIG. 3 schematically illustrates a block diagram of a system 100 for managing personal data relayed between telemedicine device 10 and a remote user 130, in accordance with some embodiments of the present invention. Telemedicine device 10 may receive data from diagnostic devices/sensors over a diagnostic device/sensor communication link 110 using Bluetooth, wireless fidelity (Wi-Fi) and/or USB (wired) connections, for example. Diagnostic devices/sensors shown in FIG. 3 may include, for example, but are not limited to a blood pressure meter 102, a pulse oximeter 104, a stethoscope 106, and a thermometer 108.

Telemedicine device 10 may communicate with remote terminal 9 via proxy server 8 over first communication link 4 and second communication link 6 for relaying personal data to a remote user 130 operating remote browser 7 on remote terminal 9 (also shown alternatively in FIG. 1).

Telemedicine device 10 may initiate as video/voice call 125 with remote user 130 over a video/voice communication link 120 such as a connection via voice over internet (VoIP), a circuit switched call, a cellular call, or a video website operating on a video/voice terminal 135. Typically, video/voice communication link 120 for relaying the video and/or voice calls may be different from first and second communication links 6 and 9 with remote user 130 at remote terminal 9. For example, the telemedicine device user may initiate a video and/or voice call using touch screen 15, camera 14, and/or microphone 19 and/or speakers 16. Communication circuitry 50 may route the video and/or voice call 125 over video/voice communication link 120 to a video screen 134 and/or website operating on a video terminal 135.

In some embodiments, upon remote user 130 receiving the call from the telemedicine device user on video terminal 135, an instruction may appear on video screen 134 to instruct remote user 130 to log onto remote terminal 9 to securely access personal data from the telemedicine device user. In response to the call initiated by the telemedicine device user or by remote user 130 requesting access to the personal data of telemedicine device user on telemedicine device 10, proxy server 8 may send a secure proxy Uniform resource locator (URL) to remote terminal 9. Upon remote user 130 activating the secure proxy URL, proxy server 8 may authenticate remote user 130 for access to the personal data of the telemedicine device user.

In some embodiments, video terminal 135 and remote terminal 9 may be located on a shared terminal.

In some embodiments of the present invention, telemedicine device 10 may communicate with a device management system 145 over a device management communication link 140. Telemedicine device 10 may store a record of all transactions on telemedicine device 10 by multiple telemedicine device users without personal data or secure personal data. In some embodiments, the record may be used to debug telemedicine device 10, for example, and the record may be viewed remotely on device management system 145.

In some embodiments of the present invention, if properly authorized, telemedicine device 10 may communicate personal data and/or records stored in memory 35, for example, with an electronic health record system (EHR) 150 via an EHR communication link 151.

Figure 4:
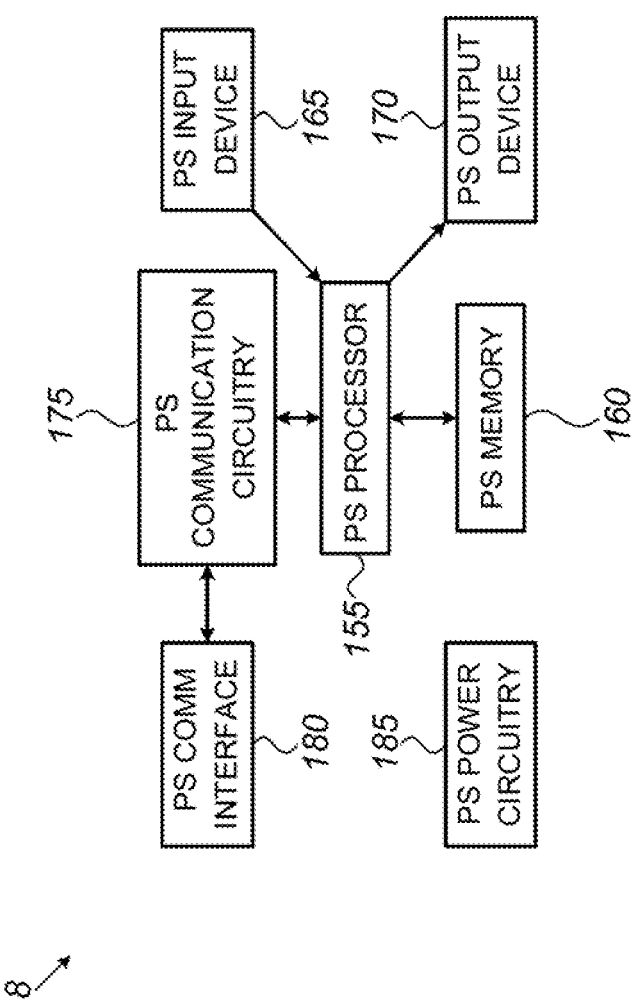
FIG. 4 is a block diagram of a proxy server, in accordance with some embodiments of the present invention.

FIG. 4 is a block diagram of proxy server (PS) 8, in accordance with some embodiments of the present invention. Proxy server 8 may include a PS processor 155, a PS memory 160, a PS input device 165, a PS output device 170, PS communication circuitry 175, PS power circuitry 185 (e.g., for powering proxy server c) a PS communication interface 180. PS communication circuitry 175 may include for example, cellular, Wi-Fi and/or Bluetooth circuitry interfaced to an antenna via PS communication interface 180, for example.

PS processor 155 may include one or more processing units, e.g. of one or more computers. PS processor 155 may be configured to operate in accordance with programmed instructions stored in PS memory 160. PS processor 155 may be capable of executing an application for managing relaying personal data between telemedicine device 10 and remote terminal 9.

PS processor 155 may communicate with PS output device 170. For example, PS output device 170 may include a computer monitor or screen. PS processor 155 may communicate with a screen of PS output device 170 to display information. In another example, PS output device 170 may include a printer, display panel, speaker, or another device capable of producing visible, audible, or tactile output.

PS processor 155 may communicate with PS input device 165. For example, input device 40 may include one or more of a keyboard, keypad, or pointing device for enabling a user to inputting data or instructions for operation of PS processor 155.

PS processor 155 may communicate with PS memory 160. PS memory 160 may include one or more volatile or nonvolatile memory devices. PS memory 160 may be utilized to store, for example, programmed instructions for operation of PS processor 155, data or parameters for use by PS processor 155 during operation, or results of operation of PS processor 155.

PS memory 160 may include a computer readable medium for storing program instructions for operation of PS processor 155. It is noted that PS memory 160 and/or any suitable data storage device communication with processor 30 may be remote from PS processor 155. PS memory 160 may store a module in the form of an installation package or packages that can be downloaded and installed for execution by PS processor 155. PS memory 160 may be utilized to store data or parameters for use by PS processor 155 during operation, or results of operation of PS processor 155.

In operation, PS processor 155 may execute a method for managing the relaying of personal data between telemedicine device 10 and remote terminal 9.

Figure 5A:
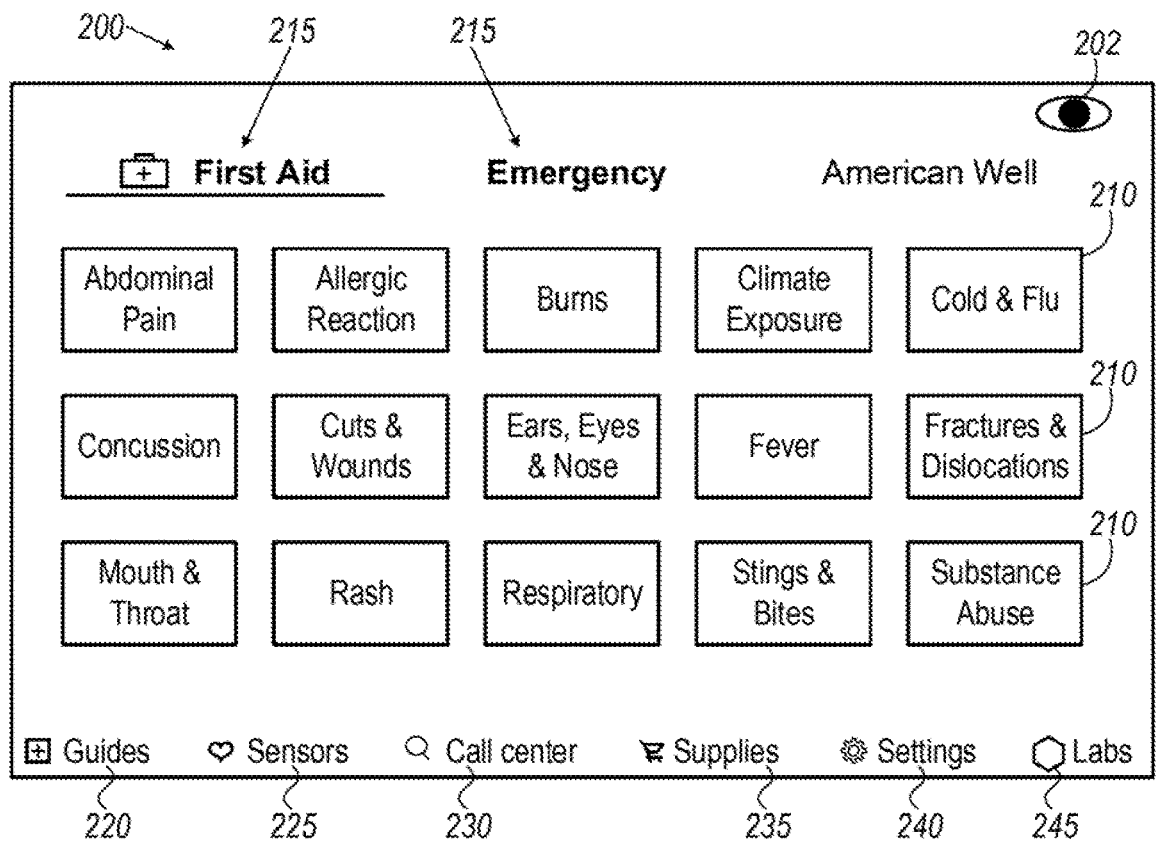
FIG. 5A illustrates a first embodiment of a graphic user interface (GUI) of a telemedicine device, in accordance with some embodiments of the present invention.
Figure 5B:
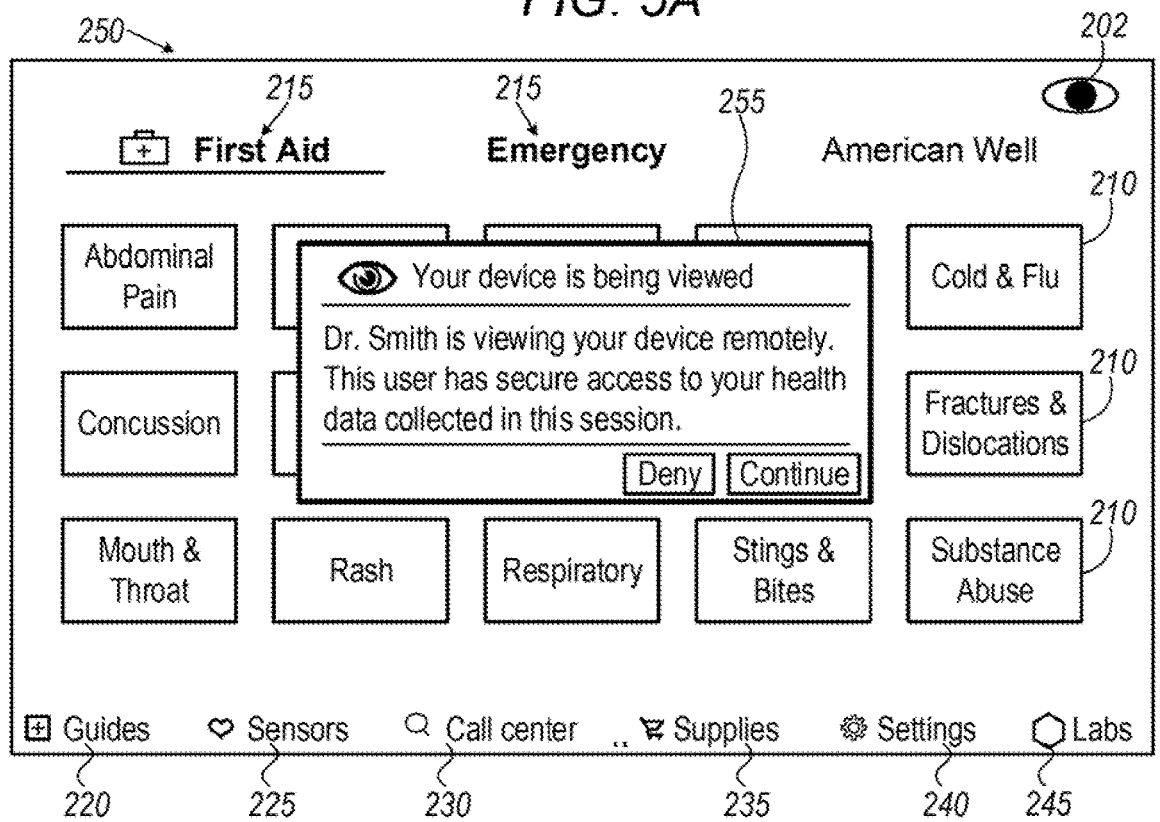
FIG. 5B illustrates a second embodiment of a graphic user interface (GUI) of a telemedicine device with an alert, in accordance with some embodiments of the present invention.

FIG. 5A illustrates a first embodiment of a graphic user interface (GUI) 200 of telemedicine device 10, in accordance with some embodiment of the present invention. The first exemplary embodiment of GUI 200 may include category indicia 215 (e.g., "First Aid" and "Emergency") for telemedicine device user to choose via touch screen 15 (e.g., using his finger, or a stylus, for example). With the "First Aid" menu chosen as shown in FIG. 5A, a sub-menu may be displayed with a variety of first aid icons 210 to choose such as "Abdominal Pain", "Allergic Reaction", "Burns", etc. as shown in FIG. 5A. GUI 200 may include a variety of menu icons such as Guide 220, Sensors 225, Call Center 230, Supplies 235, Settings 240, and Labs 245.

FIG. 58 illustrates a second embodiment of a graphic user interface (GUI) 250 of telemedicine device 10 with an alert 255, in accordance with some embodiments of the present invention. When remote user 130 requests to view the private data of the telemedicine device user, proxy server 8 may relay the authentication request to telemedicine device 10, which may pop-up on touchscreen 15 as an alert box, for example, so as to indicate to the telemedicine device user that remote user 130 is requesting to view private data (e.g., the health data collected by telemedicine device 10). In some embodiments, validating and/or allowing secure access for remote user 130 to view the personal data on remote terminal 9 may include the telemedicine device user allowing (e.g., choosing "continue" in alert 255) or denying the request (e.g., choosing "deny" in alert 255). Once the decision is made by telemedicine device 10 to authenticate remote user 130, the decision may be relayed back to proxy server 8. If access to view the personal data is denied, the proxy server 8 terminates remote user access.

In some embodiments of the present invention, telemedicine device 10 may be configured to allow access for multiple telemedicine device users. Telemedicine device 10 may identify and allow access by any suitable authentication procedure such as username/password, for example, to be entered into touch screen 15, biometric data such as fingerprints, etc., and/or facial recognition using camera 14, for example.

In some embodiments of the present invention, different types or levels of remote access may be supported by different indication levels or prompts. For example, the use of camera 14 may initiate a pop-up prompt with a request with a provider name. Access to a stored intake report may be accessed by clicking on a prompt display in the background of touch screen 15.

In some embodiments of the present invention, GUI 200 may be configured to provide a user experience, for example, where an icon 202 on touch screen 15 allows the telemedicine device user to know when remote access to telemedicine device 10 is active and the remote user accessing it. In other embodiments, icon 202 may be a permanent icon on touch screen 15. In yet other embodiments, icon 202 may use color coding. For example, a grey color in icon 202 may indicate that no one is assessing telemedicine device 10, a red color may indicate that someone is requesting remote access to telemedicine device 10, and a green color may indicate that telemedicine device 10 is being remotely accessed.

Figure 6:
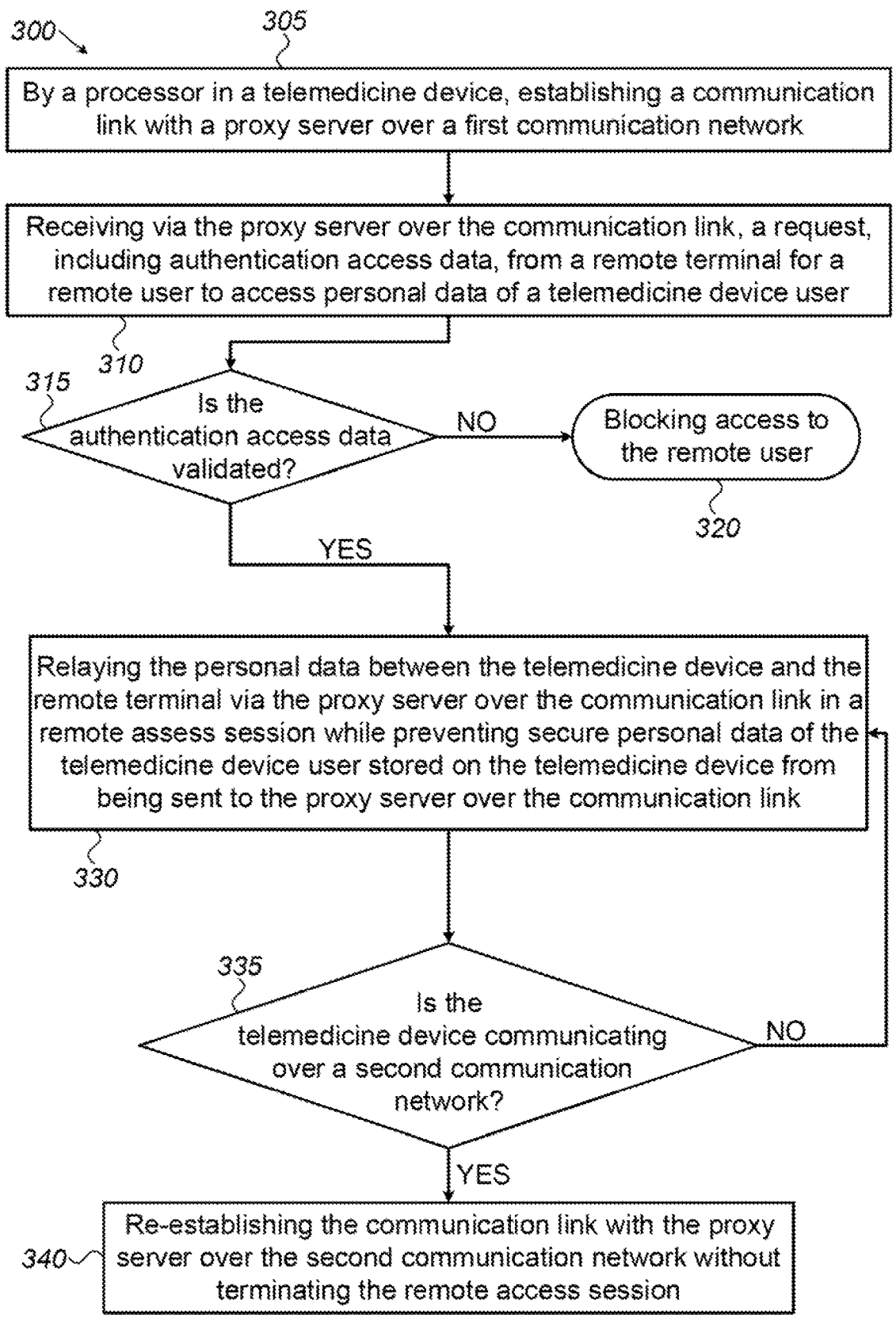
FIG. 6 is a flowchart depicting a method for a telemedicine device to securely relay personal data to a remote terminal via a proxy server, in accordance with some embodiments of the present invention.

FIG. 6 is a flowchart depicting method 300 for telemedicine device 10 to securely relay personal data to remote terminal 9 via proxy server 8, in accordance with some embodiments of the present invention. Method 300 may be executed by processor 30 of telemedicine device 10.

Method 300 may include establishing 305 a communication link 4 with proxy server 8 over a first communication network (e.g., Wi-Fi, wired, cellular, etc.).

Method 300 may include receiving 310 via the proxy server over communication link 4, a request, including authentication access data, from remote terminal 9 for remote user 130 to access personal data of a telemedicine device user. In some embodiments, the authentication access data may include the identity of remote user 130, the IP address of remote terminal 9, the geographic location of remote user and/or remote terminal, and cryptographic secrets associated with the remote terminal.

Method 300 may include a decision step 315 to assess whether the authentication access data is validated to allow a remote user to access the personal data on telemedicine device 10. If not, method 300 may include blocking 320 access to remote user 130. If so, method 300 may include relaying 330 the personal data between telemedicine device 10 and remote terminal 9 via proxy server 8 over the communication link in a remote assess session while preventing secure personal data of the telemedicine device user stored on telemedicine device 40 from being sent to proxy server 8 over the communication link. In some embodiments, processor 30 may generate and send an indication to proxy server 8 that the authentication access data is validated to permit remote user 10 to access the personal data on telemedicine device 10.

In some embodiments, assessing the authentication access data may include whether the remote user is listed on a whitelist or a blacklist of users, whether the geographic location of the user and/or remote terminal in within a restricted geographic region for viewing. This authentication access data may then be used by proxy server 8, telemedicine device 10, or both to validate and/or allow and/or approve access by the remote user to the personal data of the telemedicine device user.

Method 300 may include a second decision step 335 to assess if the telemedicine device communicates over a second communication network. If not, telemedicine device 10 continues relaying 330 the personal data between telemedicine device 10 and remote terminal 9 via proxy server 8 over the communication link. If not, method 300 may include re-establishing 340 the communication link with the proxy server over the second communication network without terminating the remote access session.

In method 300, the personal data relayed between the telemedicine device and the remote terminal via proxy server is encrypted.

In some embodiment of the present invention, the secure personal data of the telemedicine device user ma include protected health information (PHI) or personally identifiable information (PII) data of the telemedicine device user.

In some embodiment of the present invention, the first communication network and the second communication network may be selected from a group consisting of a wireless fidelity (Wi-Fi) network, a cellular network, a wired network, and a Bluetooth network.

In some embodiment of the present invention, establishing the communication link with the proxy server may include establishing the communication link with the proxy server in response to a call made from the telemedicine device user to the remote user.

In some embodiment of the present invention, method 300 may include alerting the telemedicine device user that the remote user requested access to the personal data.

In some embodiments of the present invention, validating the authentication access data may include allowing the telemedicine device user to approve the access to the personal data in response to alerting the telemedicine device user.

In some embodiments of the present invention, validating the authentication access data may include assessing that the remote user is not located within a restricted geographical area.

In some embodiments of the present invention, validating the authentication access data may include assessing that the remote user is not on a list of restricted users.

In some embodiments of the present invention, validating the authentication access data may include comparing an IP address of the remote terminal to an IP address associated with a remote voice communication or video communication of the remote user.

Method 300 may include requesting a secondary authentication upon assessing that the IP address of the remote terminal and the IP address associated with the remote voice communication or the video communication of the remote user do not match.

Figure 7:
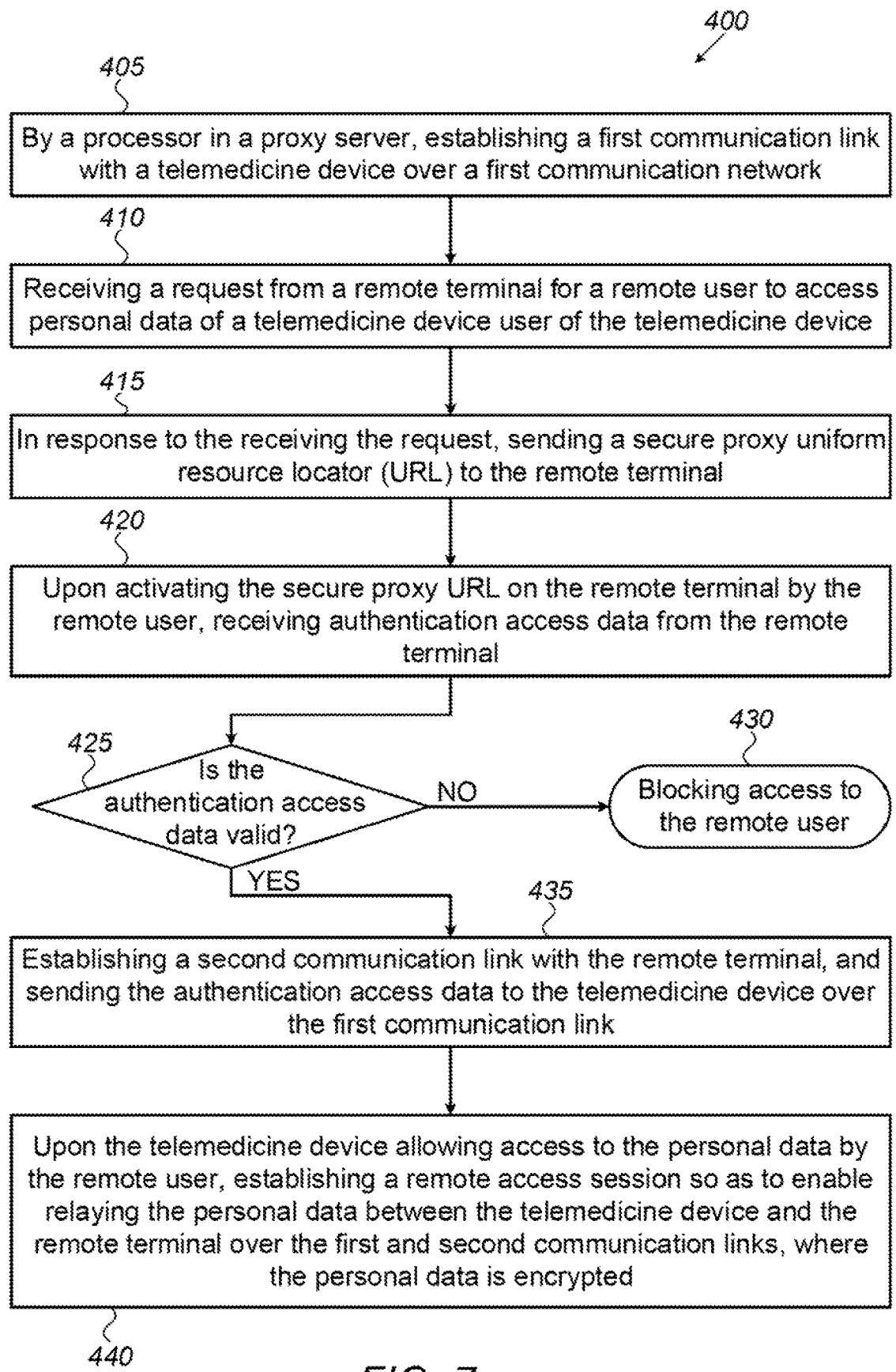
FIG. 7 is a flowchart depicting a method for a proxy server to manage relaying personal data between a telemedicine device and a remote terminal, in accordance with some embodiments of the present invention.

FIG. 7 is a flowchart depicting a method 400 for proxy server 8 to manage relaying personal data between telemedicine device 10 and remote terminal 9, in accordance with some embodiments of the present invention. Method 400 may be executed by PS processor 155 of proxy server 8.

Method 400 may include establishing 405 first communication link 4 with telemedicine device 10 over a first communication network.

In some embodiments of the present invention, method 400 may include establishing 405 first communication link 4 with telemedicine device 10 over a first communication network by establishing a mutually authenticated Transport Layer Security (TLS) socket to proxy server 8 (e.g., first communication link 4). Proxy server 8 may map telemedicine device 10 as being online.

Method 400 may include receiving 415 a request from remote terminal 9 for remote user 130 to access personal data of a telemedicine device user of telemedicine device 10.

PS processor 155 may generate a secure proxy uniform resource locator (URL) in response to receiving the request. In some embodiments, the secure proxy URL may be used only within a predefined duration to allow access by the remote user to the telemedicine device. In other embodiments, once the secure proxy URL is activated by the remote user, the secure proxy URL may not be re-used.

Method 400 may include sending 415 a secure proxy uniform resource locator (URL) to remote terminal 9 in response to the receiving the request.

Method 400 may include receiving 420 authentication access data from remote terminal 9 upon activating the secure proxy URL, on remote terminal 9 by remote user 130.

A decision step 425 assesses if the authentication access data is validated. If not, method 400 may include blocking 430 access to remote user 130. If so, method 400 may include establishing 435 a second communication link 6 with the remote terminal, and sending the authentication access data to the telemedicine device over the first communication link.

Method 400 may include establishing 440 a remote access session so as to enable relaying the personal data between telemedicine device 10 and remote terminal 9 over the first 4 and second 6 communication links upon telemedicine device 10 allowing access to the personal data by remote user 130.

In method 400, the personal data relayed between the telemedicine device and the remote terminal over the first and second communication links is encrypted.

In some embodiments of the present invention, method 400 may include upon assessing that the telemedicine device communicates over a second communication network, re-establishing the first communication link with the telemedicine device over the second communication network without terminating the remote access session.

In some embodiments of the present invention, establishing the first communication link with the telemedicine device may include establishing the first communication link in response to a call made from the telemedicine device user to the remote user.

In some embodiments of the present invention, method 400 may include terminating the remote access session and deactivating the secure proxy URL in response to the telemedicine device user or the remote user ending a call.

In some embodiments of the present invention, method 400 may include terminating the remote access session and deactivating the secure proxy URL after a predefined duration or inactivity time.

In some embodiments of the present invention, the authentication access data may include a token encrypted at the remote terminal using a public key of the telemedicine device.

In some embodiments of the present invention, the token may be signed using a key known by the proxy server.

In some embodiments of the present invention, sending the secure proxy URI, may include sending multiple unique secure proxy URLs respectively to multiple remote terminals. Multiple URLs may be used, for example, to allow access to specific providers accessing the telemedicine device.

In some embodiments of the present invention, multiple users at respective multiple remote terminals may be authenticated by different methods. For example, in response to a doctor who is logged in (e.g., after basing used a username and password for authentication) at a remote terminal may be evaluating a child using a telemedicine device. The doctor may wish to invite a parent to log on. The telemedicine device, or the proxy server, or both may send an e-mail with a secure URL to a parent to log on. In other embodiments, the telemedicine device, or the proxy server, or both may send an authentication code via a cellphone or e-mail to enter into a cellphone application, or a website.

In some embodiments of the present invention, telemedicine device 10 may allow telemedicine device user to approve one or more remote users to view or access his personal data such as via pop-up message 255. In this case, multiple authentication tarns may be sent from telemedicine device 10 and/or front proxy server 8 when may be routed to the multiple remote users over multiple communication links to permit access at respective multiple remote terminals to the personal data of the patient.

Even though the doctor may be registered with the proxy server with a username and password, the doctor may want to bring in another party (e.g., a parent, another doctor, a health care provider representative, for example) that may not be registered with an account for accessing the telemedicine device. In this manner, the additional user may be authenticated for access to the personal data without having to create an account for the additional user. The additional user may be authenticated by a secure URL sent to a specific e-mail address and/or telephone number. For added security, once the secure URL is used, the secure URL may then be invalidated and cannot be reused again so as to prevent rogue access to the patient's private data.

Stated differently, system 100 may include different mechanisms for authenticating different remote users for a given video anchor remote access session. Depending on the type of authentication mechanism used, the telemedicine device user may not need to authorize all of the remote users (e.g., with alert 255) as described above.

In some embodiments of the present invention, when a first remote user at a first remote terminal sends a request to the proxy server for a connection (e.g., a communication link) to a telemedicine device, the proxy server may establish a routing for the personal data to be relayed between the first remote terminal and the proxy server. The telemedicine device may establish a connection to the proxy server for the first remote user in response to the request.

When one or more additional remote users at, respective one or more, additional remote terminals each send a request to the proxy server for a connection to the telemedicine device, each of the one or more additional remote terminals may establish a connection with the proxy server. In response to the requests, the telemedicine device may establish one or more additional connections with the proxy server to communicate with each of the one or more additional remote terminals. In other embodiments, the telemedicine device may relay the personal data to the proxy server. The proxy server may be configured to multiplex and/or broadcast and/or relay the personal data to all of the remote terminals (e.g., the first remote terminal, and the one or more additional remote terminals). In yet some embodiments, each of the one or more additional remote users at respective one or more additional remote terminals may connect to telemedicine device 10 over different communication paths.

In some embodiments of the present invention, the content of the webpages displayed on remote browser 7 on remote terminal 9 may be formed from hypertext markup language (HTML) and Java scripts stored on proxy server 8 and the personal data stored on telemedicine device 10. PS processor 155 may combine the personal data from telemedicine device 10 with the HTML and Java scripts to form the webpages and to relay the webpage content over second communication link 6 to remote terminal 9 for remote user 130 to view on remote browser 7.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that litany modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for a telemedicine device to securely relay personal data to a remote terminal via a proxy server, the method comprising:
   by a processor in a telemedicine device, the telemedicine device including one or more diagnostic devices or sensors providing real time diagnostic measurements of a medical condition of a telemedicine device user, the real time diagnostic measurements being included in personal data of the telemedicine device user stored in the telemedicine device,
   establishing, by use of the telemedicine device processor, a communication link with a proxy server over a first communication network, the proxy server being a mere intermediary or relay between endpoint devices including the telemedicine device and a remote terminal, wherein the proxy server forwards endpoint device requests and does not itself service endpoint device requests, the communication link being a transport layer security (TLS) encrypted websocket, wherein data sent between endpoint devices via the websocket is encrypted at a sending endpoint device and decrypted at a receiving endpoint device without being decrypted at the proxy server;
   receiving, by use of the telemedicine device processor via the proxy server over the communication link, a request, including authentication access credentials, from the remote terminal for a remote user to access the personal data of the telemedicine device user;
   using the telemedicine device processor to validate the authentication access credentials of the request, wherein the proxy server not having access to the authentication access credentials and not validating the authentication access credentials;
   upon validating the authentication access credentials data to allow the remote user access to the personal data on the telemedicine device, relaying, by use of the telemedicine device processor, the personal data between the telemedicine device and the remote terminal via the proxy server over the communication link in a remote access session while preventing secure personal data of the telemedicine device user stored on the telemedicine device from being sent to the proxy server in an un-encrypted form over the communication link; and
   if the telemedicine device communicates over a second communication network, re-establishing, by use of the telemedicine device processor, the communication link with the proxy server over the second communication network without terminating the remote access session; wherein the personal data relayed between the telemedicine device and the remote terminal via the proxy server is encrypted.

2. The method according to claim 1, wherein the secure personal data of the telemedicine device user comprises protected health information (PHI) or personally identifiable information (PII) data of the telemedicine device user.

3. The method according to claim 1, wherein the first communication network and the second communication network are selected from a group consisting of a wireless fidelity (Wi-Fi) network, a cellular network, a wired network, and a Bluetooth network.

4. The method according to claim 1, wherein establishing the communication link with the proxy server comprises establishing the communication link with the proxy server in response to a call made from the telemedicine device user to the remote user.

5. The method according to claim 1, further comprising alerting the telemedicine device user that the remote user requested access to the personal data.

6. The method according to claim 5, wherein validating the authentication access credentials comprises allowing the telemedicine device user to approve or remove approval for specific individuals to access to the personal data in response to alerting the telemedicine device user.

7. The method according to claim 1, wherein validating the authentication access credentials comprises assessing that the remote user is not located within a restricted geographical area.

8. The method according to claim 1, wherein validating the authentication access credentials comprises assessing that the remote user is not on a list of restricted users.

9. The method according to claim 1, wherein validating the authentication access credentials comprises comparing an internet protocol (IP) address of the remote terminal to an IP address associated with a remote voice communication or video communication of the remote user.

10. The method according to claim 9, further comprising requesting a secondary authentication upon assessing that the internet protocol (IP) address of the remote terminal and the IP address associated with the remote voice communication or the video communication of the remote user do not match.

11. A method for a proxy server to manage relaying personal data between a telemedicine device and a remote terminal, the method comprising:
- by a processor in a proxy server;
- establishing, by use of the proxy server processor, a first communication link with a telemedicine device over a first communication network, the proxy server being a mere intermediary or relay between endpoint devices including the telemedicine device and a remote terminal, wherein the proxy server forwards endpoint device requests and does not itself service endpoint device requests, the first communication link being a transport layer security (TLS) encrypted websocket, wherein data sent between endpoint devices via the websocket is encrypted at a sending endpoint device and decrypted at a receiving endpoint device without being decrypted at the proxy server, the telemedicine device including one or more diagnostic devices or sensors providing real time diagnostic measurements of a medical condition of a telemedicine device user, the real time diagnostic measurements being included in personal data of the telemedicine device user stored in the telemedicine device;
- receiving, by use of the proxy server processor, a request from the remote terminal for a remote user to access the personal data of the telemedicine device user;
- in response to the receiving the request, sending, by use of the proxy server processor, a secure proxy authentication uniform resource locator (URL) to the remote terminal;
- upon activating the secure proxy authentication URL on the remote terminal by the remote user, receiving, by use of the proxy server processor, authentication access credentials from the remote terminal;
- using the telemedicine device to validate the authentication access credentials received from the remote terminal, wherein the proxy server not having access to the authentication access credentials and not validating the authentication access credentials;
- upon validating the authentication access credentials, establishing, by use of the proxy server processor, a second communication link with the remote terminal, and sending, by use of the proxy server processor, the authentication access credentials to the telemedicine device over the first communication link; and
- upon the telemedicine device allowing access to the personal data by the remote user, establishing, by use of the proxy server processor, a remote access session to enable relaying the personal data between the telemedicine device and the remote terminal over the first and second communication links, wherein the personal data relayed between the telemedicine device and the remote terminal over the first and second communication links is encrypted.

12. The method according to claim 11, further comprising upon assessing that the telemedicine device communicates over a second communication network, re-establishing the first communication link with the telemedicine device over the second communication network without terminating the remote access session.

13. The method according to claim 11, wherein establishing the firm communication, link with the telemedicine device comprises establishing the first communication link in response to a call made from the telemedicine device user to the remote user.

14. The method according to claim 11, further comprising terminating the remote access session and deactivating the secure proxy URL in response to the telemedicine device user or the remote user ending a call.

15. The method according to claim 11, further comprising terminating the remote access session and deactivating the secure proxy URL after a predefined duration or inactivity time.

16. The method according to claim 11, wherein sending the secure proxy URL comprises sending multiple unique secure proxy URLs respectively to multiple remote terminals.

17. The method according to claim 11, wherein the authentication access credentials comprise a token encrypted at the remote terminal, using a public key of the telemedicine device.

18. The method according to claim 17, wherein the token is signed using a key known by the proxy server.

19. A telemedicine device for securely relaying personal data to a remote terminal via a proxy server, the telemedicine device comprising:
- one or more diagnostic devices or sensors providing real time diagnostic measurements of a medical condition of a telemedicine device user, the real time diagnostic measurements being included in personal data of the telemedicine device user stored in the telemedicine device,
- a memory for storing the personal data of the telemedicine device user; and
- a processor in data communication with the one or more diagnostic devices or sensors and the memory, the processor configured to establish a communication link with a proxy server over a first communication network, the proxy server being a mere intermediary or relay between endpoint devices including the telemedicine device and a remote terminal, wherein the proxy server forwards endpoint device requests and does not itself service endpoint device requests, the communication link being a transport layer security (TLS) encrypted websocket, wherein data sent between endpoint devices via the websocket is encrypted at a sending endpoint device and decrypted at a receiving endpoint device without being decrypted at the proxy server, the processor further configured to receive via the proxy server over the communication link, a request, including authentication access credentials, from the remote terminal for a remote user to access the personal data of the telemedicine device user, the processor of the telemedicine device further configured to validate the authentication access credentials of the request, wherein the proxy server not having access to the authentication access credentials and not validating the authentication access credentials, upon validating the authentication access credentials to allow the remote user access to the personal data on the telemedicine device, the processor further configured to relay the personal data between the telemedicine device and the remote terminal via the proxy server over the communication link in a remote access session while preventing secure personal data of the telemedicine device user stored on the telemedicine device from being sent in an un-encrypted form to the proxy server over the communication link, and if the telemedicine device communicates over a second communication network, the processor further configured to re-establish the communication link with the proxy server over the second communication network without terminating the remote access session; wherein the personal data relayed between the telemedicine device and the remote terminal via the proxy server is encrypted.

20. The telemedicine device according to claim 19, wherein the secure personal data of the telemedicine device user comprises protected health information (PHI) or personally identifiable information (PII) data of the telemedicine device user.

21. The telemedicine device according to claim 19, wherein the first communication network and the second communication network are selected from a group consisting of a wireless fidelity (Wi-Fi) network, a cellular network, a wired network, and a Bluetooth network.

22. The telemedicine device according to claim 19, wherein the processor is configured to establish the communication link with the proxy server in response to a call made from the telemedicine device user to the remote user.

23. The telemedicine device according to claim 22, further comprising a video camera, and wherein the call comprises a video call.

24. The telemedicine device according to claim 19, further comprising an input device for receiving inputs from the telemedicine device user, and an output device for displaying information to the telemedicine device user.

25. The telemedicine device according to claim 24, wherein the input device and the output device comprise a touch screen.

26. The telemedicine device according to claim 24, wherein the processor is configured to alert the telemedicine device user on the output device that the remote user requested access to the personal data.

27. The telemedicine device according to claim 26, wherein the processor is configured to validate the authentication access credentials by allowing the telemedicine device user to approve or remove approval for specific individuals to access to the personal data on the input device in response to the alert.

28. The telemedicine device according to claim 19, wherein the processor is configured to validate the authentication access credentials by assessing that the remote user is not located within a restricted geographical area.

29. The telemedicine device according to claim 19, wherein the processor is configured to validate the authentication access credentials by assessing that the remote user is not on a list of restricted users.

30. The telemedicine device according to claim 19, wherein the processor is configured to validate the authentication access credentials by comparing an internet protocol (IP) address of the remote terminal to an IP address associated with a remote voice communication or video communication of the remote user.

31. The telemedicine device according to claim 30, wherein the processor is configured to request a secondary authentication upon assessing that the internet protocol (IP) address of the remote terminal and the IP address associated with the remote voice communication or the video communication of the remote user do not match.

32. The telemedicine device according to claim 19, wherein the processor is configured to enable the telemedicine device user to terminate the remote user access to the personal data on the telemedicine device.

* * * * *